(12) United States Patent
Bojrab

(10) Patent No.: US 6,696,057 B1
(45) Date of Patent: Feb. 24, 2004

(54) COMPOSITION AND METHOD FOR TREATMENT OF GASTROINTESTINAL DISORDERS AND HYPERLIPIDEMIA

(75) Inventor: Gregory G. Bojrab, Indianapolis, IN (US)

(73) Assignee: Lacpro Industries, Inc., Indianapolis, IN (US)

( * ) Notice: Subject to any disclaimer, the term of this patent is extended or adjusted under 35 U.S.C. 154(b) by 0 days.

(21) Appl. No.: 09/629,578

(22) Filed: Jul. 31, 2000

Related U.S. Application Data

(60) Provisional application No. 60/155,322, filed on Sep. 22, 1999.

(51) Int. Cl.$^7$ ................................................. A01N 63/00
(52) U.S. Cl. ................ 424/93.3; 424/93.45; 424/93.44; 424/93.4; 435/42; 435/252.9; 435/253.4
(58) Field of Search ........................... 424/93.44, 93.45, 424/93.3, 93.4; 435/252.9, 253.4, 42

(56) References Cited

U.S. PATENT DOCUMENTS

| | | |
|---|---|---|
| 3,988,440 A | 10/1976 | Bogdanov |
| 4,156,019 A | 5/1979 | Kondratenko et al. |
| 4,410,549 A | 10/1983 | Baker |
| 4,425,366 A | 1/1984 | Sozzi et al. |
| 4,710,379 A | 12/1987 | Kawai et al. |
| 4,806,368 A | 2/1989 | Reddy |
| 4,837,036 A | 6/1989 | Baker et al. |
| 5,185,321 A | 2/1993 | Link et al. |
| 5,385,743 A * | 1/1995 | Van Der Schaft ............. 426/42 |
| 5,409,718 A | 4/1995 | Klaver et al. |
| 5,413,785 A | 5/1995 | Nanji |
| 5,531,988 A | 7/1996 | Paul |
| 5,591,428 A | 1/1997 | Bengmark et al. |
| 5,635,202 A | 6/1997 | Ford |
| 5,709,857 A | 1/1998 | Morelli et al. |
| 5,716,615 A | 2/1998 | Cavaliere Vesely et al. |
| 5,827,552 A | 10/1998 | Mainzer et al. |
| 5,849,289 A | 12/1998 | Dobrogosz et al. |
| 5,895,648 A | 4/1999 | Cavaliere Vesely et al. |
| 5,902,578 A | 5/1999 | Halpin-Dohnalek et al. |
| 5,902,743 A | 5/1999 | Luchansky et al. |
| 5,932,214 A | 8/1999 | Lobb et al. |
| 6,008,027 A | 12/1999 | Langner |

FOREIGN PATENT DOCUMENTS

| | | |
|---|---|---|
| EP | 0856259 A | 8/1998 |
| FR | 2656799 A | 7/1991 |

* cited by examiner

*Primary Examiner*—Irene Marx
(74) *Attorney, Agent, or Firm*—Michael A. Swift; Doreen J. Gridley; Ice Miller

(57) ABSTRACT

A probiotic composition and method for the treatment of gastrointestinal disorders, hyperlipidemia and autoimmune diseases. The probiotic composition comprises a culture having *lactobacillus bulgaricus* and *streptococcus thermophilus* lactic acid bacteria and a carbohydrate enriched media, whereby the culture and media are combined and allowed to ferment until a desired ratio of the *lactobacillus bulgaricus* and *streptococcus thermophilus* organisms as well as a desired number of total organisms per dose are achieved. The method of the present invention comprises the steps of providing a probiotic composition of the present invention and administering the composition to a patient having at least one of gastrointestinal disorders, hyperlipidemia or autoimmune diseases.

8 Claims, 1 Drawing Sheet

COMPOSITION AND METHOD FOR TREATMENT OF GASTROINTESTINAL DISORDERS AND HYPERLIPIDEMIA

RELATED APPLICATIONS

This application is filed as a continuation of a provisional patent application filed under 37 CFR 1.53(B)(2), application Ser. No. 60/155,322, filed on Sep. 22, 1999, entitled "Composition and Method for Treatment of Ulcerative Colitis," invented by Gregory G. Bojrab. That application is incorporated herein by this reference.

BACKGROUND

1. Field of the Invention

The present invention relates to the field of treatment of gastrointestinal disorders, hyperlipidemia and autoimmune diseases. More particularly, the present invention relates to a probiotic composition having lactic acid bacteria of the genius/species *lactobacillus bulgaricus* and *streptococcus thermophilus*, and a method of treatment using the same.

2. Background of the Invention

Gastrointestinal disease includes many disorders, including but not limited to, inflammatory bowel diseases such as ulcerative colitis and Crohn's disease, infectious enteritis (viral, bacterial, parasitic), antibiotic associative diarrhea, *clostridium difficile* colitis, microscopic or lymphocytic colitis, collagenous colitis, colon polyps and familial polyp syndromes (e.g., familial polyposis syndrome, Gardner's Syndrome), *helicobacter pylori*, irritable bowel syndrome, nonspecific diarrheal illnesses, and intestinal cancers.

The cause of many of these diseases is unknown. Such is the case with inflammatory bowel disease ("IBD"), the general term for diseases that cause inflammation in the intestines. For example, ulcerative colitis ("UC") is an IBD that causes inflammation of the mucosa lining of the large intestine. The inflammation usually occurs in the rectum and lower part of the colon, but it may affect the entire colon.

The most common symptoms of UC include abdominal pain, tenesmus, fecal urgency, and bloody diarrhea. A person with UC may also experience fatigue, weight loss, loss of appetite, rectal bleeding, and loss of body fluids and electrolytes. Although UC is generally not itself fatal, a more severe form of the disease may lead to the formation of toxic megacolon leading to bowel perforations or bowel obstruction. UC may also increase the risk of colon cancer depending on the duration, extent and severity of the disease.

Despite the prevalence of IBD, including UC and Crohn's disease, no theories regarding the cause have yet been proven. In fact, as stated in U.S. Pat. No. 5,932,214, even the broader category of diseases known as IBD have "no cure, and exact causes of IBD are not yet understood." (Col. 1, lines 40–41). Yet, advances in UC have shown, however, that it is possible to control the inflammation without knowing the etiology of the disease. Present methods of treatment for UC depend upon the extent of the disease and the severity of the symptoms. To distinguish the amount of colonic surface involved in the inflammation process, UC is divided into subgroups, including ulcerative proctitis, proctosigmoiditis, left sided UC and pancolitis. The locations of each of these subgroups of UC are illustrated in FIG. 1.

Present treatments for gastrointestinal disorders, in general, and for UC specifically, rely on drug therapy and, where such drug therapy is not effective, surgery is required. For example, initial treatment for mild to moderate UC may include the 5-ASA agents, including sulfasalazine, oral or rectal mesalamine, or olsalazine as well as conventional corticosteroid enemas. Another treatment for UC is disclosed in U.S. Pat. No. 5,932,214. This method of treatment involves administration of an antibody, polypeptide or other molecule recognizing VLA-4 (very late antigen-4). Patients with persistent mild to moderate symptoms of active UC, in spite of these therapies (treatment refractory), may require conventional corticosteroids orally. Patients with still persistent symptoms or those with severe UC may require immunosuppressive agents such as azathioprine or 6-MP. Cyclosporin may be considered for those who do not respond. If conventional treatment is successful, remission is usually maintained with sulfasalazine and/or oral or rectal mesalamine or olsalazine, and, in some cases with azathioprine/6-MP.

Crohn's disease like UC is an inflammatory disease of the intestinal tract, but unlike UC, may involve any part of the GI tract, from mouth to anus. The terminal ilcum is a common site of involvement in active Crohn's disease and may result in malabsorption syndromes. Symptoms include diarrhea, abdominal pain, nausea, weight loss, and growth retardation. Active disease may lead to intestinal obstruction, bleeding, fistula formation, rectal abscesses, bowel perforation and peritonitis, and increased susceptibility to bowel cancer.

Treatment of Crohn's disease involves use of 5-aminosalycilic acids, corticosteroids, and immunosuppressive drugs. Antibiotics are necessary for infections and surgery may be required for refractory Crohn's or the complications that may develop from the disease. 5-ASA compounds may cause headache, nausea, fatigue, abdominal pain, worsening diarrhea, and in some cases, hypersensitivity reactions leading to rash, fever hepatitis, pneumonitis, hemolytic anemia, and bone marrow suppression.

Long term use of corticosteroids may cause Cushing's Syndrome hyperglycemia, acne, muscle weakness, osteoporosis, and cataract formation, among other things. Immunosuppressive agents may cause hepatic toxicity, bone marrow suppression, and pancreatitis among other things. Response to therapy is measured by improvement in clinical signs/symptoms of the disease along with improvement in disease activity on gastrointestinal imaging, using endoscopy and barium x-ray studies.

With respect to infectious enteritis, there are a variety of viruses, bacteria, and parasites that can infect the digestive tract and cause sudden and sometimes violent symptoms, including nausea/vomiting, diarrhea (sometimes bloody), abdominal pain and cramping, fever, weakness, and loss of appetite. Among the viral causes, most are due to the Rotaviruses and the enteric caliciviruses such as Norwalk virus. Among the bacterial causes, Salmonella, Shigella, and Camphylobacter are the most common, but other pathogens like pathogenic *E. Coli*, Vibrio, and Yersinia can occur in endemics both inside and outside the United States. Parasitic infection can be due to protozoal organisms like *Entamoeba histolytica*, Giardia, and Cryptosporidium.

Treatment of these infections include general supportive measures like bed rest, hydration, and nutritional support. Some require antibiotics or antiparasitic agents. These drugs can cause allergic reactions and can affect the normal bowel flora and cause superinfections with harmful bacteria like *Clostridium difficile*. Some may also effect other organ systems like the liver and kidneys. Clinical improvement can be monitored by the white blood count, and clearing of the offending pathogen on serial stool analysis.

Antimicrobial agents are responsible for 25% of drug induced diarrhea. The rates of antibiotic associated diarrhea ("AAD") vary from 5 to 39% depending on the specific type of antibiotic used. The mechanism of AAD may be due to functional disturbance of intestinal carbohydrate or bile acid metabolism, an allergic or toxic effect on the intestinal mucosa, a pharmacologic effect on motility, or a disruption of the normal intestinal flora causing an overgrowth of harmful bacteria like *Clostridium difficile, Clostridium perfinges, Staphylococcus aureus, Klebsiella oxytoca,* Candida species, or Salmonella species. About 10 to 20% of all cases of AAD are caused by *Clostridium difficile,* an anaerobic bacteria that secretes 2 enterotoxins, A and B, which can induce a severe colitis of the intestinal lining. Symptoms, at one end of the spectrum include a mild diarrhea, which resolves after discontinuation of the antibiotic, to severe disease causing high fever, leukocytosis, abdominal pain, profuse diarrhea, hypoalbuminemia, dehydration, and electrolyte disturbances. In rarer cases, toxic megacolon with perforation and death may occur.

The impact of AAD is reflected by higher medical costs, increased hospital stays, and increased rates of comorbidities. Treatment involves discontinuing the antibiotic, general supportive measures, bed rest, hydration, electrolyte and nutritional support, and in some cases, treatment with other antibiotics like metronidazole and vancomycin, to help restore the normal balance of the intestinal flora. In the more severe cases, surgery and colectomy may be necessary. Parameters used to measure improvement include resolution of symptoms, restoration of fluid and electrolyte balance, normalization of the white blood count, and clearing of toxins on serial stool analysis. In some cases, endoscopic evaluation of mucosal damage is necessary.

Microscopic or lymphocytic colitis and collagenous colitis may represent variants of the same disease. The disease is characterized by a waxing and waning watery diarrhea that usually affects middle-aged females. Colonoscopy shows normal appearance of the mucosa but biopsy shows infiltration of the lamina propria with inflammatory cells and intraepithelial lymphocytes. It is only in collagenous colitis that a subepithelial band of collagen is present. The pathogenesis of the disorder remains a mystery but there is evidence, much like UC and Crohn's disease, that the inflammatory process may be triggered by a luminal agent. The disease is treated much like IBD with 5-ASA drugs and corticosteroid. 5-ASA products may cause headache, nausea, fatigue, abdominal pain and worsening diarrhea. Hypersensitivity reactions may lead to rash, fever, hepatitis, pneumonitis, hemolytic anemia, and bone marrow suppression. Long term use of corticosteroids may cause Cushing's disease, hyperglycemia, acne, muscle weakness, osteoporosis, and cataracts, among other things.

The majority of colorectal cancers, regardless of etiology, are believed to arise from adenomatous polyps. These polyps protrude from the mucosa and are visible endoscopically. Regular lower GI screening and removal of polyps remains, by far, the best way to prevent colon cancer. Unfortunately, colon cancer still remains the second leading cause of cancer death in the U.S. primarily because of an unsatisfactory adherence to a regimented screening program. Certain hereditary syndromes (like Familial Polyposis) are characterized by the appearance of thousands of adenomatous polyps throughout the large bowel. If left surgically untreated, colorectal cancer will develop in almost all patients prior to age 40. To prevent colon cancer in these individuals, a total colectomy is usually required. There is currently no other hard and fast way to prevent colon polyps and thus colorectal cancer, but dietary factors, like enhancing fiber and lowering saturated fat intake, might help. Nonsteroidal anti-inflammatory drugs like sulindac and celecoxib hold some promise. Many times though, these nonsteroidal agents may produce adverse GI side effects, renal failure, edema, and hypertension.

Irritable bowel syndrome ("IBS") is the most common gastrointestinal disease in clinical practice, and although not life threatening, it causes great distress. The patient with IBS may present with one of 3 clinical variants: patients with spastic colitis complain primarily of chronic abdominal pain and constipation. A second group has chronic intermittent diarrhea, often without pain, and a third group has features of both and complain of alternating constipation and diarrhea. The cause of the disease is thought to be due to an altered intestinal motility and increased visceral perception leading to reflex intestinal motor activity. Significant psychologic disturbances may be seen in some patients with IBS. Depression, hysteria, and obsessive compulsive traits are common. Fiber supplements, tranquilizers, and anticholinergic agents are the mainstay of treatment. Unfortunately, no specific drug or dietary regimen affords good relief in all patients, and, thus, a number of therapeutic maneuvers need to be tried. Response to treatment is based solely on relief of distressing symptoms. There are no laboratory studies used to monitor IBS.

Nonspecific diarrheal illnesses usually fall into one of five categories:

1. Osmotic: pancreatic insufficiency, bacterial overgrowth, celiac disease, lactase deficiency, Whipples disease, short bowel syndrome, abetalipoproteinemia;
2. Secretory: carcinoid syndrome, Zollinger Ellison syndrome, vasoactive intestinal peptide secreting pancreatic adenomas, medullary carcinoma of the thyroid, villus adenoma of the rectum;
3. Inflammatory: radiation induced colitis, eosinophilic gastroenteritis;
4. Altered bowel motility: neurogenic diseases;
5. Facticious: laxative abuse.

Treatment and monitoring vary according to the specific cause of the diarrhea.

*Helicobacter pylori* is a micro-aerophilic gram negative bacillus that invades the gastric mucosa inducing an inflammatory response in the epithelial cell layer causing an infiltration of polymorphonuclear leukocytes. It can cause gastritis that can lead to erosions and even ulceration of the stomach and duodenum. It is the most common cause of ulcer disease in the U.S. Eradication of this organism usually requires a proton pump inhibitor in combination with clarithromycin and either amoxicillin or metronidazole. For many patients, this combination is poorly tolerated and gastrointestinal side effects are common. Antibiotic associated diarrhea along with hypersensitivity reactions can also occur. Eradication of *H. pylori* can be confirmed with either UGI endoscopy with biopsy and special staining for *H. pylori* or by the breath urea nitrogen test.

Hyperlipidemia is detected by finding an elevated cholesterol or triglyceride in fasting plasma. There are 6 types that have been described: I, Ia, IIb, III, IV, and V, and are distinguished by the pattern of lipoprotein elevation in plasma. Each type may be inherited or secondary to other disorders like diabetes mellitus or hypothyroidism. Left untreated, hyperlipidemia can lead to atherosclerotic vascular disease or in some cases acute pancreatitis. Treatment involves a low fat diet, exercise, restriction of alcohol, and lipid lowering drugs. The pharmacologic agents used include the "statins" (which may cause constipation, hepatitis, myositis, and GI disturbances), bile acid sequestrants (which may cause constipation, heartburn, nausea, and bloating), nicotinic acid (which may cause flushing, GI distress, or hyperuricemia), and fibrates (which may cause cholelithiasis, hepatitis, or myositis). Monitoring response usually involves checking fasting plasma LDL, HDL, and triglycerides levels.

Autoimmune disease are characterized by production of either antibodies that react with host tissue or immune effector T cells that are autoreactive to endogenous self peptides. Genetic factors likely play a role in the genesis toward auto antibody formation or in the case of Major Histcompatability Complex antigen association with autoimmune diseases via presentation of self or foreign peptides that stimulate inappropriate antiself response. Examples of autoimmune diseases include systemic lupus crythematosus, rheumatoid arthritis, and the vasculitis syndromes.

Treatment of these conditions usually include the use of corticosteroids and immunosuppressive agents. Long term use of corticosteroids may cause Cushing's syndrome, hyperglycemia, acne, muscle weakness, osteoporosis, cataracts, among other things. Immunosuppressive drugs may cause hepatic toxicity, bone marrow suppression, and pancreatitis, among other things. Monitoring of response is based on improvement in clinical signs/symptoms, improvement in parameters of inflammation like the westergren sedimentation rate and c reactive protein levels, and in some cases, reduction in blood levels of auto antibodies.

Generally, conventional treatment methods for most gastrointestinal disorders and autoimmune diseases are expensive for the patient. In addition, while the symptoms may be relieved by conventional treatments, there are known side effects resulting from conventional treatments. For example, the side effects associated with treatment of UC using 5-ASA agents include nausea, vomiting, heartburn, diarrhea, and headache. For immunosuppressive agents, side effects include pancreatitis, fever, rash, arthralgia, nausea, leukopenia, infection, and hepatitis. Side effects resulting from surgery relate to problems common to the use of any invasive procedure, QOL issues, and complications. Further, many current treatment methods do not appear to play a beneficial role, such as reduction in the risk of colon cancer.

Recently, a number of diseases are being treated by probiotics. The term "probiotic" implies use of bacteria which performs beneficial functions for the human organisms when they are present and alive in viable form.

Consider, for example, the composition of U.S. Pat. No. 3,988,440 for treatment of gastritis, and for gastric and duodenal ulcers. This particular composition contains 4–5.5% lactic acid bacteria or, more specifically, *lactobacillus bulgaricus*, which is cultivated in a soya media. Kawai, et al., U.S. Pat. No. 4,710,379, discloses an agent that contains bacteria cells obtained from microorganisms belonging to the genius streptococcus, but not the species *thermophilus*. Kawai, et al., also claims the method for stimulating growth of intestinal lactic acid flora by administering a microorganism belonging to the genius streptococcus to a person recognized as being deficient in intestinal lactic acid bacteria.

Cavaliere Veseley, et al., U.S. Pat. No. 5,716,615, discloses a method of treatment of gastrointestinal disorders and for treatment of hypercholesterolemia. The composition contains 10–95% of *streptococcus thermophilus* and 90–5% *l. plantarum*, and *l. sasei*, and other bacteria (see Col. 2, line 30–Col. 3, line 12). Cavaliere Veseley, et al., also suggests treatment for chronic hepatitis, high cholesterol, and irritable bowel syndrome with this composition.

Paul, U.S. Pat. No. 5,531,988, discloses an invention which comprises a bacteria and whey-containing composition, which is a mixture of an immunoglobulin and a bacterium, such as lactobacilli or bifidobacterium or mixtures thereof. This composition is used to treat diarrhea, constipation, and gas/cramps.

Ford, U.S. Pat. No. 5,636,202, discloses microencapsulated lactobacilli bacteria orally administered to treat or present antibiotic associated or other chronic or acute diarrhea. Ford suggests use of *lactobacillus bulgaricus*. Interestingly, the claims of Ford are directed only to treatment of skin infections.

Each of these probiotic treatments is limited in its application and effectiveness. It is desired to treat the aforementioned gastrointestinal and autoimmune diseases and hyperlipidemia in an effective and cost efficient manner using a single probiotic composition. Therefore, a new composition and method of treatment for gastrointestinal disorders, hyperlipidemia and autoimmune diseases is needed that is effective in reducing symptoms, reasonable in cost to the patient, does not exhibit significant adverse side effects, and which may be beneficial in reducing the risk of colon cancer. Of course, it is also desirable that the composition be easy to manufacture and deliver to the patient.

SUMMARY

In accordance with the present invention, a probiotic composition and method for the treatment of gastrointestinal disorders, hyperlipidemia and autoimmune diseases is provided that solves the deficiencies inherent in traditional treatments of gastrointestinal diseases, hyperlipidemia and autoimmune diseases. The present invention provides an effective treatment for gastrointestinal disorders, hyperlipidemia and autoimmune diseases that avoids adverse side effects, is reasonable in cost for the patient, and may be beneficial in reducing the risk of colon cancer. Further, the present invention is relatively easy to manufacture and deliver to the patient.

In accordance with the present invention, a probiotic composition for the treatment of gastrointestinal disorders, hyperlipidemia and autoimmune diseases is provided. The probiotic composition comprises a mixture having *lactobacillus bulgaricus* and *streptococcus thermophilus* lactic acid bacteria. The probiotic composition further comprises a carbohydrate enriched media whereby the mixture and media are combined and allowed to ferment until a desired ratio of the *lactobacillus bulgaricus* and *streptococcus thermophilus* organisms as well as a desired number of total organisms per dose are achieved. The desired ratio of *lactobacillus bulgaricus* and *streptococcus thermophilus* organisms ranges from about 1:1 to 10:1. The desired number of total organisms per dose ranges from about $1 \times 10^6$ to about $2 \times 10^{12}$.

The present invention further includes a method for treating gastrointestinal disorders, hyperlipidemia and autoimmune diseases using a probiotic composition. The method comprises the steps of providing a probiotic composition comprising a mixture of *lactobacillus bulgaricus* and *streptococcus thermophilus* lactic acid bacteria. The composition further comprises a carbohydrate enriched media where the mixture and the media are combined and allowed to ferment until a desired ratio of *lactobacillus bulgaricus* and *streptococcus thermophilus* organisms as well as a desired number of total organisms per dose are achieved. Next, the probiotic composition is administered to a patient.

DETAILED DESCRIPTION

Figure 1:
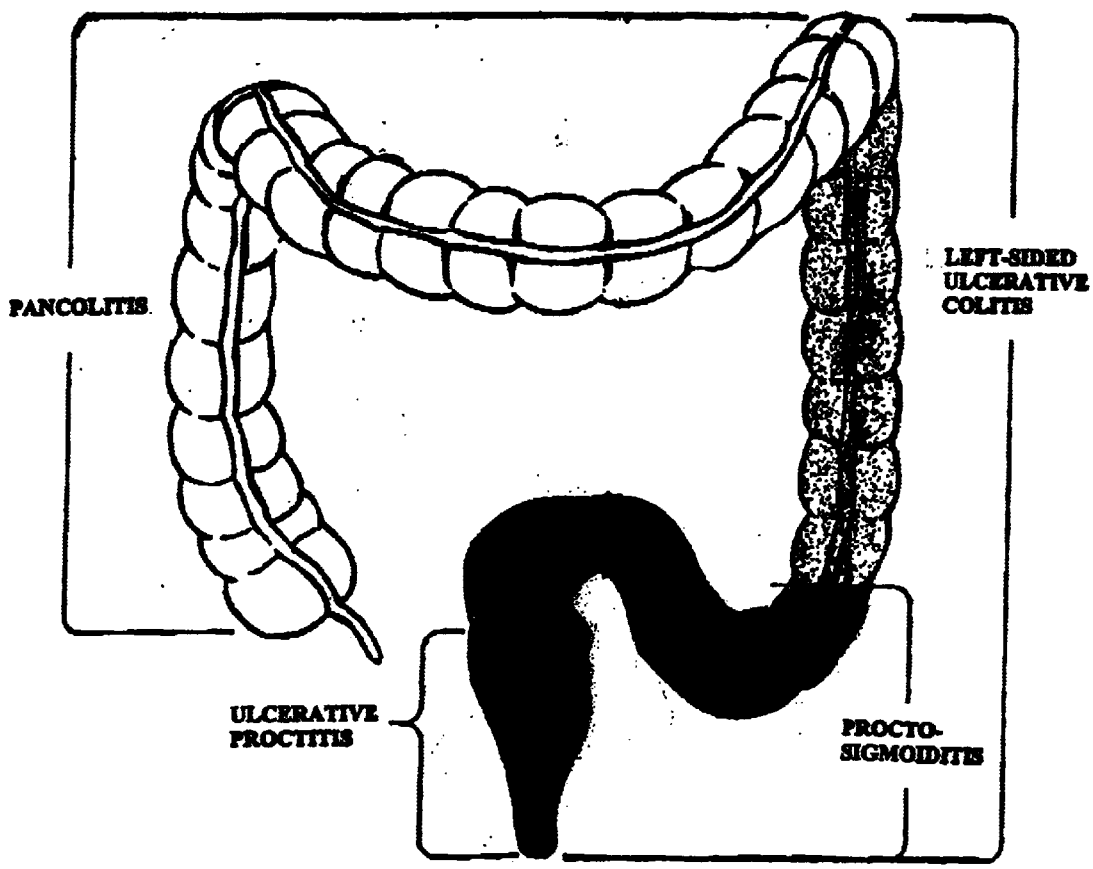
FIG. 1 shows a diagrammatic view of the large intestines of a human indicating the locations of various subgroups of ulcerative colitis.

In accordance with the present invention, a probiotic composition for the treatment of gastrointestinal disorders, hyperlipidemia and autoimmune diseases is provided. The probiotic composition comprises a mixture. The mixture comprises *lactobacillus bulgaricus* and *streptococcus thermophilus* lactic acid bacteria. The mixture may be in the form of a culture. The probiotic composition further includes a carbohydrate enriched media whereby the mixture and media are combined and allowed to ferment until a desired ratio of the *lactobacillus bulgaricus* and *streptococcus thermophilus* organisms, as well as a desired number of total organisms per dose are achieved. The probiotic composition's desired ratio of *lactobacillus bulgaricus* and *streptococcus thermophilus* organisms range from 1:1 to about 10:1. One particular embodiment of the present invention includes a desired ratio of *lactobacillus bulgaricus* to *streptococcus thermophilus* organisms of about 9:1.

The present invention's desired number of total organisms per dose range from about $1 \times 10^6$ to about $2 \times 10^{12}$. One embodiment of the present invention includes the desired number of total organisms per dose of about $5 \times 10^{10}$.

The carbohydrate enriched media includes any such media as is common in the art. One embodiment of the present invention includes a carbohydrate enriched media that is a dairy product. Any dairy product may be appropriate, but milk is particularly useful as the media.

The probiotic composition can take the final form of either a liquid, solid, or semi-solid. For example, the probiotic composition may be a set or creamy yogurt. The probiotic composition may also be lyophilized and separated into specific dosing units. The dosing units may be packaged in one of several forms including but not limited to packets, capsules, tablets, or caplets. Any other packaging form as is common in the art may be utilized.

The present invention also includes a method for treating gastrointestinal disorders, hyperlipidemia and autoimmune diseases using a probiotic composition of the present invention. The method comprises the steps of providing a probiotic composition, the probiotic composition comprising a mixture, the mixture comprising *lactobacillus bulgaricus* and *streptococcus thermophilus* lactic acid bacteria. The composition further comprises a carbohydrate enriched media whereby the mixture and media are combined and allowed to ferment until a desired ratio of the *lactobacillus bulgaricus* and *streptococcus thermophilus* organisms, as well as a desired number of total organisms per dose are achieved. The method further comprises administering the probiotic composition to a patient.

The method of the present invention further comprises selecting a dosing form of the probiotic composition and determining an initial dosing strength and initial dosing frequency. The effectiveness of the probiotic composition in treating the patient is also determined. Adjusting both the dosing strength and the dosing frequency may be required to effectuate positive results in the patient. The efficacy of the probiotic composition is determined by at least one option chosen from evaluating the improvement of the patient's clinical symptoms, or evaluating medically standard objective parameters as appropriate for a particular disorder. Such medically standard objective parameters include, but are not limited to, gastrointestinal imaging using, for example, endoscopy and barium x-ray studies, biopsy, histopathology, restoration of fluid and electrolyte balance, normalization of white blood count, serial stool analysis, and checking fasting plasma LDL, HDL and triglycerides.

The probiotic composition may be prepared by combining a starter culture in a carbohydrate enriched media. The starter culture comprises *lactobacillus bulgaricus* and *streptococcus thermophilus* lactic acid bacteria. The combination of starter culture and media is allowed to ferment. During the fermenting process, temperature and pH of the combination is monitored and controlled as is well known in the art. The fermentation process is halted upon achieving a desired ratio of *lactobacillus bulgaricus* to *streptococcus thermophilus* organisms and a desired number of total organisms per dose. The probiotic composition may be packaged for delivery in this post-fermentation state. Alternatively, the probiotic composition may be concentrated after fermentation is complete and then lyophilized prior to packaging. Prior to concentrating and lyophilizing the probiotic composition, the fermented end product can be packaged as a yogurt as is typical in the art. After concentrating and lyophilizing, the probiotic composition can be packaged into desired dosing units. The packaged dosing units may be in any suitable form as is common in the art and can include, but not be limited to packets, capsules, caplets, or tablets.

One embodiment of the present invention has been used to successfully treat a 42 year old male with severe distal ulcerative colitis. The patient had been previously unresponsive to three different 5-ASA products including Rowasa, sulfasalazine, and olsalazine. Even though an initial response was achieved with rectally administered corticosteroids, relapses continued to occur when repeated attempts were made to taper therapy. Moreover, over-the-counter probiotics were tried, both in a commercial yogurt form and in a tablet form, but were not successful in treating the patient's disease.

However, a dramatic and immediate result was achieved when the present invention was used to treat the patient's distal ulcerative colitis. The probiotic composition of the present invention was administered orally twice daily. Each dose contained approximately $5.4 \times 10^{10}$ organisms. The probiotic composition contained *lactobacillus bulgaricus* and *streptococcus thermophilus* in a ratio of 9:1. As of July 2000, the patient remains in clinical, endoscopic, and histologic remission. The patient has been off all other medications since starting therapy utilizing the probiotic composition of the present invention. The probiotic composition of the present invention remains well tolerated and has proven by far to be a preferred treatment over conventional therapy, both in composition and in delivery method.

As can be readily seen, the present invention eliminates the deficiencies associated with traditional compositions and methods of treating gastrointestinal diseases, hyperlipidemia and autoimmune diseases. The significant benefits of the present invention include effective treatment of the gastrointestinal diseases, hyperlipidemia and autoimmune diseases, as well as an avoidance of traditional side effects associated with current treatments. Further, due in large part to the relatively simple manufacturing processes and inexpensive raw materials, the present invention is much less costly to the patient than traditional approaches to treatment of gastrointestinal and autoimmune diseases and hyperlipidemia. Although other advantages may be found and realized and various modifications may be suggested by those skilled in the art, it is understood that the present invention is not to be limited to the details given above, but rather may be modified within the scope of the appended claims.

I claim:

1. A fermented probiotic composition for the treatment of gastrointestinal disorders, and hyperlipidemia, the composition comprising:
   a.) a mixture of *Lactobacillus bulgaricus* and *Streptococcus thermophilus* lactic acid bacteria; and
   b.) a carbohydrate containing media, the fermented probiotic composition comprising *Lactobacillus bulgaricus* bacteria and *Streptococcus thermophilus* bacteria in a ratio of about 9:1 and the number of *Lactobacillus bulgaricus* bacteria per dose is about $5 \times 10^{10}$.

2. The probiotic composition of claim 1, wherein the carbohydrate containing media is a dairy product.

3. The probiotic composition of claim 2, whereby the probiotic composition is a yogurt.

4. The probiotic composition of claim 3, whereby the yogurt is a lyophilized concentrate.

5. The probiotic composition of claim 4, whereby the lyophilized concentrate is packaged into dosing units, the packaged dosing units being at least one form chosen from packets, capsules, tablets, or caplets.

6. The probiotic composition of claim 1, whereby the probiotic composition is a lyophilized concentrate.

7. The probiotic composition of claim 6, whereby the lyophilized concentrate is packaged into dosing units, the packaged dosing units being at least one form chosen from packets, capsules, tablets, or caplets.

8. The probiotic composition of claim 1, whereby the probiotic composition is a liquid, solid, or semi-solid.

* * * * *

UNITED STATES PATENT AND TRADEMARK OFFICE
CERTIFICATE OF CORRECTION

PATENT NO. : 6,696,057 B1
APPLICATION NO. : 09/629578
DATED : February 24, 2004
INVENTOR(S) : Gregory G. Bojrab It is certified that error appears in the above-identified patent and that said Letters Patent is hereby corrected as shown below:

Title Page #73 should read
--Assignee: LacPro Industries, LLC, Indianapolis, IN (US) --

Signed and Sealed this

Second Day of October, 2007

JON W. DUDAS
*Director of the United States Patent and Trademark Office*